July 24, 1973 G. DE RUITER Plant Pat. 3,377
ROSE PLANT
Filed Feb. 23, 1972
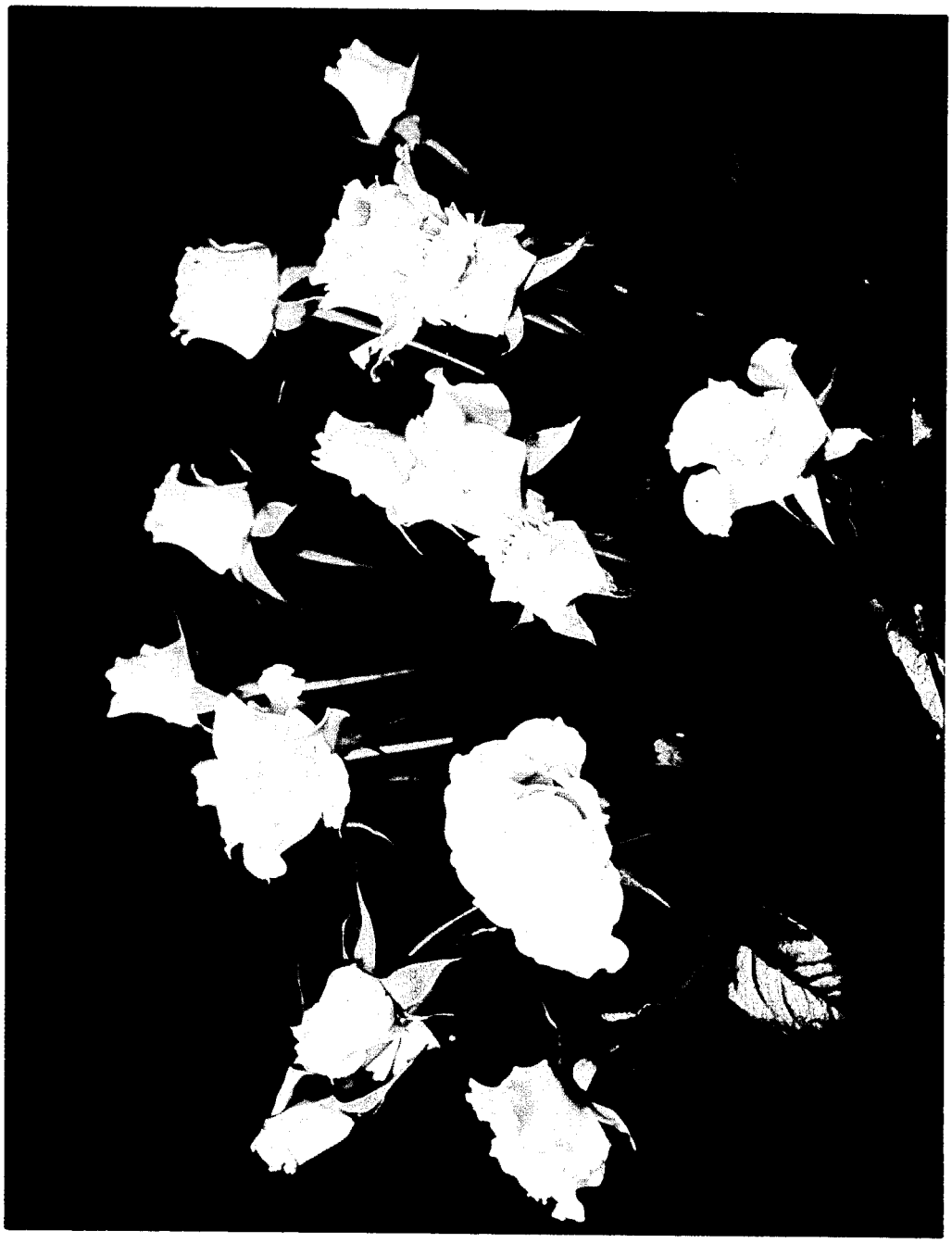

United States Patent Office

Plant Pat. 3,377
Patented July 24, 1973

3,377
ROSE PLANT

Gijsbert de Ruiter, Hazerswoude, Netherlands, assignor to Carlton Rose Nurseries, Carlton, Oreg.

Filed Feb. 23, 1972, Ser. No. 228,780
Int. Cl. A01h *5/00*
U.S. Cl. Plt.—24 1 Claim

ABSTRACT OF THE DISCLOSURE

A rose plant of the floribunda class, particularly for greenhouse growing, which was originated by crossing "Dr. A. J. Verhage," as the seed parent, with an unnamed seedling as the pollen parent.

BACKGROUND OF DISCLOSURE

The present invention relates to a new and distinct variety of rose plant of the floribunda class, particularly for greenhouse growing for cut flowers, which was originated by me by crossing "Dr. A. J. Verhage," as the seed parent, with an unnamed seedling as the pollen parent.

The primary objective of this breeding was to produce a new rose variety which would grow tall in the greenhouse for cut flowers and would provide the distinctive and desirable characteristics suitable for this purpose.

Asexual reproduction of my new variety at Hillsboro, Oreg., shows that the characteristics come true to form and that the distinguishing characteristics hold through succeeding propagations by budding.

BRIEF DESCRIPTION OF DRAWINGS

The accompanying drawing shows typical specimens of the growth and flower of my new variety in different stages of development and as depicted in color as nearly true as it is possible to make the same in color illustrations of this character.

DETAILED DESCRIPTION OF DISCLOSURE

The following is a detailed description my new variety, with color terminology in accordance with the Dictionary of Color by A. Maerz and M. Rea Paul.

Type: Hardy; bush; greenhouse; seedling; for cut flowers.
Class: Floribunda.
Propagation: It does hold its distinguishing characteristics through succeeding propagations by cuttings, grafting, budding.

*Flower*

Locality where grown: Hillsboro, Oreg.
Flowers borne: Rounded pyramidal cluster on strong, medium length stems.
Quantity of bloom: Abundant in greenhouse.
Continuity: Continuous.
Fragrance: Slight; spicy.

Bud:
- *Peduncle.*—Medium green; almost smooth; few hairs, prickles.
- *Before calyx breaks.*—Size: medium. Form: short; pointed; globular; with foliaceous appendages.
- *As calyx breaks.*—Color: Jasmine, Plate 9, K–4.
- *As first petal opens.*—Small size. Form: short; pointed. Color: Outside: Sunflower Dandelion, Plate 9, L–4; inside: Golden Glow, Plate 9, L–6.

- *Opening.*—It does open up well.

Bloom:
- *Size when fully open.*—Small, 3 inches to 4 inches.
- *Petalage.*—Double (with stamens showing), from 20 to 30 petals; arranged regularly.
- *Form.*—Cupped; becoming flat; petals remaining at first tightly rolled outward; becoming later at maturity loosely rolled outward.

Petals:
- Thick, with inside satiny velvety; outside velvety.
- *Shape.*—Outer: round, with no notches. Intermediate: ovate.

This description of a newly opened flower was made from a rose grown in August 1971 at Hillsboro, Oreg.

- *Color.*—Outer petal: Outside surface: Jasmine, Plate 9, K–4; inside surface: Forsythia, Plate 9, K–6. Intermediate petal: Outside surface: Apricot yellow, Plate 9, K–5; inside surface: Golden Glow, Plate 9, L–6. Inner petal: Outside surface: Apricot yellow, Plate 9, K–5; inside surface: Golden Glow, Plate 9, L–6.

This description was made from a rose that was open in a greenhouse in August 1971 at Hillsboro, Oreg. for three days.

- *Color.*—Outer petal: Outside surface: Sunflower, Dandelion, Plate 9, L–4; inside surface: Sunflower or Dandelion, Plate 9, L–4. Inner petal: Outside surface: Sunflower or Dandelion, Plate 9, L–4; inside surface: Apricot yellow, Plate 9, K–5.
- *General color effect.*—Newly opened flower: Jasmine, Plate 9, K–4. Three days open: Slightly darker than Sunflower or Dandelion, Plate 9, L–4; but not as dark as Plate 9, L–5.

*Behavior*: Persists; retains color regardless of temperatures.
*Flower longevity*: Cut roses grown in greenhouse kept at living room temperatures 7 days in August.

*Reproductive organs*

Stamens: Many, arranged regularly.
Filaments: Many; medium long. Color: yellow.
Anthers:
- Open at various times; medium large.
- *Color.*—Orange yellow.
- Occasionally in anther fused with a petaloid.

Pollen: Abundant.
Pistils: Medium yellow stigma.
Styles: Even; very short, thin; bunched.
Stigma: Yellow.
Ovaries: All enclosed.
Hips: Short; flat; smooth, thin; green.
Sepals: Permanent; medium long; straight spear shaped.
Seeds: Medium amount; medium size.

*Plant*

Foliage:
- *Leaves.*—Compound of 3, 5, 7; normal abundant; medium size; leathery; glossy.
- *Leaflets.*—Shape: ovoid; with apex acuminate; base round; simply serrate, serration very fine on base.
- *Color.*—Mature—Upper surface: shiny green; under surface: bronze green to grey green. Young—Upper surface: reddish green; under surface: bronze green.

*Rachis (the supporting stem of the compound leaf).*—Medium weight. Upper side: slightly hairy, prickly; under side: hairy, prickly, few thorns.

*Stipules.*—Medium long; narrow; medium points; turning out at an angle of less than 45°.

*Disease.*—Resistance comparable to the average variety growing under the same cultural conditions.

Growth:

*Habit.*—Upright, branched.

*Growth.*—Moderate, vigorous.

*Canes.*—Medium weight.

*Main stems.*—Dull. Color: green.

*Thorns.*—Several at 90° or slightly recurved. Color: green.

*Hairs.*—None.

*Branches.*—Color: green.

*Thorns.*—Several at 90° or slightly recurved. Color: green.

*Hairs.*—None.

*New shoots.*—Color: Reddish green with thorns with reddish base.

*Prickles.*—Several; straight. Color: light.

*Hairs.*—Few. Color: light.

I claim:

1. A new and distinct variety of rose plant of the floribunda class substantially as herein shown and described, characterized particularly as to its hardy upright branched growth for cut flowers, with the novelty of the blooms characterized by distinct shades of yellow which hold well indoors, and have a slight spicy fragrance.

No references cited.

ROBERT E. BAGWILL, Primary Examiner